United States Patent [19]

Albrecht et al.

[11] 4,041,164

[45] Aug. 9, 1977

[54] FUNGICIDAL DISPERSIONS OF CARBOXYLIC ACID AMIDES

[75] Inventors: Konrad Albrecht, Fischbach, Taunus; Heinz Frensch, Frankfurt am Main; Kurt Härtel, Hofheim, Taunus, all of Germany

[73] Assignee: Hoechst Aktiengesellschaft, Frankfurt am Main, Germany

[21] Appl. No.: 511,120

[22] Filed: Oct. 2, 1974

[30] Foreign Application Priority Data

Oct. 4, 1973  Germany .............................. 2349908
June 26, 1974  Germany .............................. 2430625

[51] Int. Cl.$^2$ .............................................. A01N 9/22
[52] U.S. Cl. ..................................... 424/263; 424/269; 424/270; 424/272; 424/276; 424/277; 424/278; 424/283; 424/285; 424/320; 424/324; 424/331
[58] Field of Search ............... 424/263, 276, 270, 272, 424/269, 273, 283, 285, 320, 324

[56] References Cited

U.S. PATENT DOCUMENTS

| 3,249,499 | 5/1966 | von Schmeling et al. | 424/276 |
| 3,632,821 | 1/1972 | Scherer et al. | 424/283 |
| 3,833,520 | 9/1974 | Tirpak et al. | 424/78 |

OTHER PUBLICATIONS

Chemical Abstracts, vol. 78 (1973) p. 107011s.
Chemische Berichte, 46 (1913) pp. 451-454.

*Primary Examiner*—V. D. Turner
*Attorney, Agent, or Firm*—Curtis, Morris & Safford

[57] ABSTRACT

Fungicidal dispersions comprising a carboxylic acid amide, other than pyracarbolide, as the fungicidally-active ingredient and an aluminum chelate of a polynuclear hydroxy-quinone as a crystal growth stabilizer, dispersed in a paraffinic mineral oil, a liquid triglyceride, or a liquid ester formed between a $C_1$–$C_{12}$ monoalcohol and a $C_2$–$C_{10}$ mono- or di-carboxylic acid.

8 Claims, No Drawings

FUNGICIDAL DISPERSIONS OF CARBOXYLIC ACID AMIDES

German Offenlegungsschrift No. 2,301,922 describes fungicidal dispersions of 2-methyl-5,6-dihydropyran-3-carboxylic acid anilide (pyracarbolide) which comprise a content of paraffinic mineral oils, liquid triglycerides and/or liquid esters of monoalcohols having from 4 to 12 carbon atoms. These additives not only remarkably improve the effect of pyra-carbolide on rust diseases, but also extend the activity range to Colletotrichum species such as Colletotrichum lindemuthianum, the causative agent of bean anthracnose, or Colletotrichum coffeanum, the causative agent of coffee berry disease (CBT).

It has now been found that by means of the additives described in the above German Offenlegungsschrift the efficiency of other plant fungicides of the carboxylic acid anilide series is extended and improved as well.

The present invention therefore relates to fungicidal dispersions containing as dispersion medium a member of the groups consisting of paraffinic mineral oils, liquid triglycerides and/or liquid esters of $C_1$ to $C_{12}$ monoalcohols and $C_2$ to $C_{10}$ carboxylic acids, these esters containing at least 8 and, in the case of esters of monovalent acids, a maximum of 12, in the case of esters of bivalent acids a maximum of 32 carbon atoms, and, as active ingredient, a compound of the formula

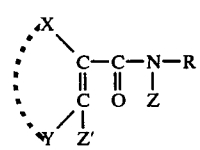

I wherein X and Y, together with the —C=C—group, form a five- to six-membered partially or totally unsaturated carbocyclic or heterocyclic ring system which, in addition to the radical Z', may contain halogen ($C_1$ to $C_4$) alkyl or alkoxy, oxymethylene and/or phenyl as further substituents, Z is hydrogen, straight or branched alkyl or halo-alkyl having from 1 to 6 carbon atoms, Z' is hydrogen, halogen or ($C_1$ to $C_4$) alkyl, R is a radical of the formula

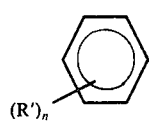

IIa or

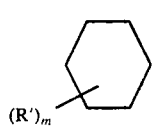

IIb where R' is identical or different alkyl or alkoxy having from 1 to 4 carbon atoms or dioxymethylene, $m$ is an integer of from 0 to 3 and $n$ is also an integer of from 0 to 3 or, if the

group is a dihydropyran ring

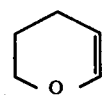

and Z is methyl, an integer of from 1 to 3.

The ring systems represented in the formula I by the group

are generally known. By way of example the following are mentioned: heterocyclic rings such as the furan, pyran, dihydrofuran, dihydropyran, oxazole, triazole, thiadiazole, thiazole, dioxan, dithiane, 4H-thiapyran, 4H-thiapyran dioxide, pyridine ring systems, or carbocyclic substances such as the cyclopentene, cyclohexene, norbornadiene and phenyl rings as well as 5,6-dihydro-1,4-oxathiine or -oxathiine-4,4-dioxide.

Thus the >C=C< double bond needs not be a localized ethylenic double bond but may be part of a delocalized π-electron system. The radical Z' is preferably halogen (Cl) or ($C_1$ to $C_4$) alkyl; methyl being preferred. Besides the radical Z', the carbocyclic or heterocyclic ring system may also contain other substituents such as halogen, low molecular weight alkyl or alkoxy, oxymethylene or phenyl. Preferred further substituents are halogen (at an aromatic ring) and methyl or ethyl (at a heterocyclic ring). Examples of the cited ring system are the following radicals:

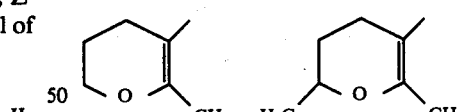

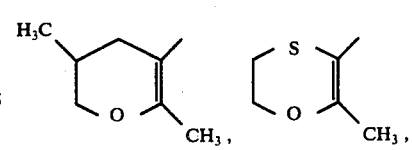

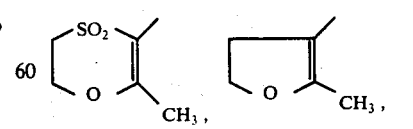

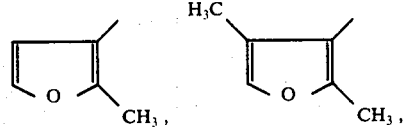

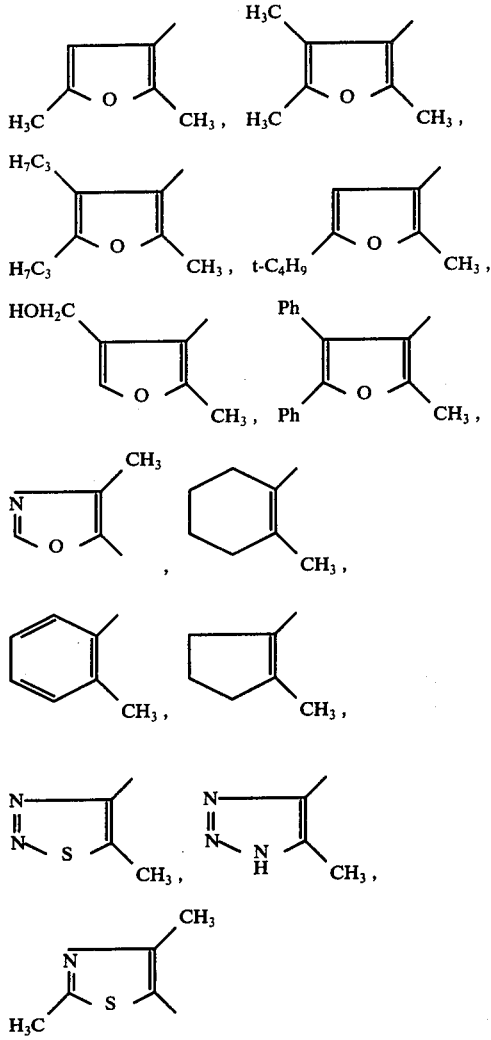

Z is advantageously hydrogen, preferred integers are: $n = 0$ or $1$ and $m = 0$.

The following compounds useful in the present invention are mentioned by way of example 2-methyl-4,5-dihydrofuran-3-carboxanilide,
2-methyl-5,6-dihydropyran-3-carboxanilide,
2-methyl-5,6-dihydro-4H-thiapyran-3- and -1,1-dioxide-3-carbox-anilide,
2-methyl-furan-3-carboxanilide,
4-methyl-1,3-oxazole-5-carboxanilide,
2-methyl-cyclohexene-(1)-1-carboxanilide,
2-methyl-cyclopentene-(1)-1-carboxanilide,
5-methyl-1,2,3-thiadiazole-4-carboxanilide,
5-methyl-1,2,3-triazole-4-carboxanilide,
2-ethyl-5,6-dihydro-(4H)-pyran-3-carboxanilide,
3-methyl-pyridine-2-carboxanilide,
2,6-dimethyl-5,6-dihydro-(4H)-pyran-3-carboxanilide,
2,5-dimethyl-5,6-dihydro-(4H)-pyran-3-carboxanilide, and the corresponding -carbox-2'-methyl-anilides, the corresponding -carbox -3'-methyl-anilides,
the corresponding -carbox-4'-methyl-anilides,
the corresponding -carbox-2'-ethyl-anilides,
the corresponding -carbox-3'-ethyl-anilides,
the corresponding -carbox-4'-ethyl-anilides,
the corresponding -carbox-2'-isopropyl-anilides,
the corresponding -carbox-3'-isopropyl-anilides,
the corresponding -carbox-4'-isopropyl-anilides,
the corresponding -carbox-2'-methoxy-anilides,
the corresponding -carbox-3'-methoxy-anilides,
the corresponding -carbox-4'-methoxy anilides,
the corresponding -carbox-2-ethoxy-anilides,
the corresponding -carbox-3'-ethoxy-anilides,
the corresponding -carbox-4'-ethoxy-anilides,
the corresponding -carbox-propoxy- and -isopropoxy-anilides or
the corresponding -carbox-3', 4'-dioxymethylene-anilides.

Especially preferred are the 2-methyl-5,6-dihydropyran-3-carboxylic acid anilides, substituted in the anilide ring, especially the o-, m-, p-methylanilides, the o-, m-, p-ethylanilides, the o-, m-, p-propyl- or -isopropylanilides, the o-, m-, p-methoxy-anilides, the o-, m-, p-ethoxy-anilides, the o-, m-, p-propoxy- or -isopropoxy-anilides, and the corresponding anilides of 2-methyl-5,6-dihydro-1,4-oxathiine-3-carboxylic acid and 2-methyl-5,6-dihydro-1,4-oxathiine-4,4-dioxide-3-carboxylic acid and, for both oxathiine-carboxylic acids also the anilides unsubstituted in the anilide ring.

The cited compounds are either known (cf. German Offenlegungsschrift No. 1,914,954 and U.S. Pat. No. 3,294,499), or they are analogous compounds which may be obtained according to the processes described therein. The compounds substituted in the anilide ring may be obtained in analogy to the unsubstituted compounds described, for example by reacting correspondingly substituted carboxylic acid chlorides with known substituted anilines.

Suitable dispersion media used in the dispersions of the invention are, for example, 1. straight chain or branched $C_8$ to $C_{25}$ paraffins having boiling points above 140° C, preferably above 260° C, for example octane, nonane, decane, undecane, dodecane, tridecane, tetradecane, pentadecane, hexadecane, their mixtures, or mixtures thereof with higher boiling homologs, such as hepta-, octa-, nonadecane, eicosane, heneicosane, docosane, tricosane, tetracosane, pentacosane, and the branched chain isomers thereof;

2. liquid triglycerides, for example vegetable oils such as rape-seed oil, arachis oil, sunflower oil, cotton seed oil;

3. liquid esters of $C_1$ to $C_{12}$ monoalcohols with $C_2$ to $C_{10}$ carboxylic acids, such esters containing at least 8 and, in the case of esters of monobasic acids, at most 12 carbon atoms, and, in the case of esters of dibasic acids, at most 32 carbon atoms. Suitable esters are, for example, those of aliphatic $C_6$ to $C_{10}$ carboxylic acids, for example of caproic acid, capric acid, caprylic acid and pelargonic acid; or of aromatic carboxylic acids such as benzoic acid, toluylic acid, salicylic acid and phthalic acid. Suitable alcohol components in these esters are, for example, butanol, n-octanol, i-octanol, dodecanol, cyclopentanol, cyclohexanol, cyclooctanol, or benzyl alcohol. Esters to be used in the dispersions of the invention are thus, for example, benzyl acetate, caproic acid ethyl ester, pelargonic acid ethyl ester, benzoic acid methyl or ethyl ester, salicylic acid methyl, propyl, or butyl ester, preferably, however, diesters of phthalic acid with saturated aliphatic or alicyclic $C_1$ to $C_{12}$ alcohols, such as phthalic acid dimethyl ester, dibutyl ester, diisooctyl ester, didodecyl ester, dicyclopentyl ester, dicyclohexyl ester, or dicylcooctyl ester.

The dispersions of the invention are prepared by known methods, e.g. by grinding the active compound dispersed in the dispersion medium in a colloid mill, ball mill, sand mill, and preferably in grinding ball mills, optionally with the addition of further usual formulation auxiliaries such as emulsifiers, dispersion media, wetting agents or adhesives.

The content of active ingredient of the dispersions is in the range of from 5 to 50% by weight, preferably 15 to 30% by weight. Highly concentrated dispersions containing 50% by weight of active ingredient or slightly less are used as ultra low volume (ULV) preconcentrates. They may contain further additions of formulations auxiliaries but are unsuitable for direct application owing to their high viscosity; they have to be diluted prior to application. Suitable diluents for this purpose are, in the first place, the mineral oil, triglyceride or ester used for preparing the dispersion to which emulsifiers, wetting agents, adhesives, or dispersing agents may be added according to requirements. It is of course also possible to use mixtures of mineral oils, trigylcerides and/or esters for making dispersions ready for application. In general, the proportion of emulsifiers and dispersing agents in the total dispersion is below 20%, wetting agents and adhesives can be added to the dispersion in an amount of up to 5%.

Suitable emulsifiers and dispersing agents are substituted alkylphenol polyglycol ethers, such as octyl-, nonyl-, or triisobutylphenol polyglycol ether, natural fatty alcohol polyglycol ethers as well as polyglycol ethers of synthetic alcohols, preferably isotridecanol polyglycol ether, furthermore fatty acid polyglycol esters, and mixtures of ethoxylated substances, optionally in combination with calcium salts of alkyl-benzene or paraffin-sulfonic acids and chlorinated paraffin-sulfonic acids.

Suitable wetting agents are, for example, emulsifiers such as oxethylated alkylphenols, salts or alkyl- or arylsulfonic acids or salts of oleylmethyl tauride, for example sodium salt of oleylmethyltauride.

In the preferred range of from 15 to 30% of active ingredient, the dispersions in accordance with the invention are readily pourable. Their viscosity in the range of application is below 5, preferably below 3 poises, depending on the content of active ingredient, and they can be dispersed in any desired proportion both in water and paraffinic mineral oils. Depending on the degree of dilution, they can be applied according to the low volume or ultra low volume process by aeroplanes or by soil application devices.

The compounds of formula I in the form of a dispersion have a pronounced tendency to crystal growth depending on the solvent and the storage temperature (samples in which the active compound is ground to a particle size of less than 5 microns may contain crystals of a length of over 50 microns after a prolonged storage at 50° C). The dispersions in accordance with the present invention should therefore be applied soon after their preparation. Surprisingly, an excellent stability in storage can be obtained by adding to the dispersions an aluminum chelate compound, preferably an aluminum chelate of an aromatic polynuclear quinone containing hydroxy groups of which one is in periposition to an oxygen atom of the quinone grouping, such as naphthazarin, quinizarin, chrysazin, and preferably alizarin. (The preparation of such aluminum chelates is described in Chemisch Berichte 46, page 451 et seq.) The addition of chelates of this type strongly reduces crystal growth. In a test of long duration at 50° C the active particles still had an average particle size below 5 microns even after 2 month's storage. A storage under these conditions is equivalent to a storage for 2 years at normal temperature.

The amounts of aluminum chelate necessary for stabilizing the oil dispersions of the invention are, in general, in the range of from about 0.2 to about 5% by weight, preferably 0.4 to 1% by weight, calculated on the total formulation. Amounts higher than 5% may also be added, but offer no additional advantage.

Aluminum chelate compounds can be added to the dispersion either per se or in the form of their starting components (aluminum salts or aluminum hydroxide, perferably aluminum acetate, and an aromatic quinone, preferably alizarin) prior to preparation. In the latter case the chelate compounds are formed during the grinding of the formulation components, which can be perceived by the change in color from yellow orange to red. When the single components are used aluminum compound and quinone are added in stoichiometric amounts or, for the sake of simplicity, in equal amounts by weight.

The stabilized oil dispersions of the compounds of formula I have the same biological effect as the unstabilized freshly prepared dispersions. Owing to their long stability in storage at +50° C they comply with international standards and ensure reliable application and safe combating result. Expecially successful is the stabilization process according to this invention in the case of those compounds of formula I where X and Y are closed to form a heterocycle and where R is an optionally substituted phenyl ring.

The following examples illustrate the invention. In the biological examples the infestation of untreated plants is equal to 100.

EXAMPLES OF FORMULATION

EXAMPLE 1

In a grinding ball mill operated with quartz beads having a diameter of 1 to 2 mm the following mixture was ground until the particles had a size of less than 5 microns:
- 15.8 weight % of o-iodine-benzoic acid anilide, ind.-grade (corresponding to 15 weight % of pure active substance)
- 8.0 weight % of oseylphenol-polyglycol ether (Triton X-207 Rohm & Haas, U.S.A.)
- 3.0 weight % of isotridecanol-polyglycol ether (Genapol X-080 Hoechst AG)
- 73.2 weight % of an aliphatic mineral oil (Essobayol 90 Esso AG).

EXAMPLE 2

As described in Example 1,
- 15.5 weight % of 2-methyl-5,6-dihydropyran-3-carboxylic acid-(o-isopropyl-anilide), ind. grade (corr. to 15 weight % of pure active substance)
- 7.8 weight % of Triton X-207
- 3.0 weight % of Genapol X-080
- 73.7 weight % of Essobayol 90 were ground.

At a storage time of 2 months at 50° C, there was heavy crystal growth of the finely ground active substance having a grain size below 5 microns, crystals of a length of 300 microns being formed. When 0.4 weight % of alizarin and 0.4 weight % of aluminum hydroxyacetate were added and ground with a corresponding decrease of the Essobayol amount, the crystal growth was completely stopped (the storage conditions being the same).

EXAMPLE 3

There were ground as indicated in Example 1
- 15.8 weight % of 2-methyl-5,6-dihydropyran-3-carboxylic acid (o-ethyl-anilide), ind. grade (corr. to 15 weight % of pure active substance)
- 7.3 weight % of Triton X-207
- 3.2 weight % of Genapol X-080
- 73.7 weight % of Essobayol 90 or Shellsol K (Shell AG).

Under the storage conditions of Example 2 crystals of up to 80 microns were formed. When 0.5 weight % of alizarin and 0.5 weight % of aluminum hydroxy-acetate were incorporated during the grinding operation with corresponding decrease of the Essobayol amount, the original grain size distribution of below 5 microns was maintained (the storage conditions being the same).

EXAMPLE 4

There were ground as indicated in Example 1:
- 15.5 weight % of 2-methyl-5,6-dihydropyran-3-carboxylic acid (m-ethoxy-anilide), ind. grade (corr. to 15 weight % of pure substance)
- 8.0 weight % of Triton X-207
- 2.8 weight % of Genapol X-080
- 73.7 weight % of Essobayol 90.

When 0.5 weight % of alizarin and 0.5 weight % of aluminum hydroxy-acetate were incorporated during the grinding operation and with corresponding decrease of the Essobayol amount, the crystal growth could be prevented also in this case.

EXAMPLE 5

There were ground as indicated in Example 1:
- 15.8 weight % of 2-methyl-5,6-dihydropyran-3-carboxylic acid (o-ethoxy-anilide), ind. grade (corr. to 15 weight % of pure active substance)
- 8.0 weight % of Triton X-207
- 3.0 weight % of Genapol X-080
- 73.2 weight % of Essobayol 90.

The crystal growth occurring on storage at 50° C could be completely prevented as in Example 3, when the dispersion was ground with addition of 0.4 weight % of alizarin and 0.4 weight % of aluminum hydroxy-acetate.

EXAMPLE 6

There were ground as indicated in Example 1:
- 15.8 weight % of 2,5-dimethyl-furan-3-carboxylic acid-cyclo-hexylamide
- 8.0 weight % of Triton X-207
- 3.0 weight % of Genapol X-080
- 73.2 weight % of Essobayol 90.

EXAMPLE 7

There were ground as indicated in Example 1:
- 15.8 weight % of 2-methyl-5,6-dihydropyran-3-carboxylic acid (3',4'-dioxymethylene-anilide)
- 8.0 weight % of Triton X-207
- 3.0 weight % of Genapol X-080
- 73.2 weight % of Essobayol.

On storage at 50° C, crystals having a length of 45 microns had formed already after one month. By adding 0.5 weight % of alizarin and 0.5 weight % of aluminum hydroxy-acetate during the grinding operation with decrease of the Essobayol amount to 72.2 weight %, this crystal growth was practically completely suppressed.

EXAMPLE 8

There were ground as indicated in Example 1: 14.3 weight % of 2,5-dimethyl-furan-3-caboxylic acid anilide, ind. grade
- 7.6 weight % of Triton X-207
- 6.0 weight % of calcium salt of dodecylbenzenesulfonic acid (Phenylsulfonat, Hoechst AG)
- 3.75 weight % of oleyl alcohol polyglycol ether (Genapol 0-40, Hoechst AG)
- 3.75 weight % of stearyl alcohol polyglycol ether (Genapol S-040, Hoechst AG)
- 64.6 weight % of Essobayol 90.

On storage at 50° C, this dispersion showed very heavy crystal growth. After 2 months, crystals of up to 500 microns were visible, causing the loss of dispersion properties as in the Examples before, so that the product became biologically inactive. By adding, 0.8 weight % of alizarin and 0.8 weight % of aluminum hydroxy-acetate with corresponding decrease of the Essobayol amount, the growth of the active substance particles was considerably reduced.

EXAMPLE 9

There were ground as indicated in Example 1:
- 20 weight % of 2-methyl-5,6-dihydro-1,4-oxathiine-3-carboxanilido-4,4-dioxide (oxycarboxine)
- 10 weight % of Triton X-207
- 3 weight % of Genapol X-080 and
- 73 weight % of Essobayol 90.

The formulation had a viscosity of 4 poises at room temperature and was well dispersible in water or could be diluted with other paraffinic oils. On storage at 50° C, the product showed crystals of a diameter of 30 microns after 8 weeks, and of a diameter of 50 microns after 3 months. The solid matter, after this time, was only poorly dispersible in water and flocculated rapidly. The biological activity was considerably reduced.

EXAMPLE 10

There were ground as indicated in Example 1:
- 20 weight % of oxycarboxine
- 10 weight % of Triton X-207
- 3 weight % of Genapol X-080
- 1 weight % of aluminum-alizarin lake and 72 weight % of Essobayol 90

The dispersion was readily pourable, had a viscosity of 4 poises and was very well dispersible in water and paraffinic oils. It had the same properties as the dispersion according to Example 9 and met all technological requirements. After a 3 month storage at 50° C no crystal growth could be detected. The dispersion was stable and could be applied as before storage. The biological results of the stored product corresponded to those of the freshly prepared product (within the limit of error).

EXAMPLE 11

There were ground as indicated in Example 1:
- 20 weight % of oxycarboxine
- 10 weight % of Triton X-207
- 3 weight % of Genapol X-080
- 0.5 weight % of alizarin
- 0.5 weight % of aluminum acetate and
- 72 weight % of Essobayol 90.

During the grinding operation, the originally orange-yellow dispersion turned red. The dispersion had the same properties and the same stability to storage as the dispersion prepared according to Example 10.

EXAMPLE 12

There were ground as indicated in Example 1:
20 weight % of oxycarboxine
10 weight % of Genapol X-080
69 weight % of phthalic acid isooctyl ester and
0.5 weight % of aluminum-alizarin lake.

Also this dispersion, because of the presence of the aluminum lake, was stable to storage contrary to an identical formulation prepared without the dye. The dispersion was pourable, dispersion in water and oil and had a very good biological activity.

EXAMPLE 13

There were ground as indicated in Example 1:
20 weight % of 2-methyl-5,6-dihydro-1,4-oxathiine-3-carboxanilide (carboxine)
9 weight % of Triton X-207
4 weight % of Genapol X-080
73 weight % of Essobayol 90.

The dispersion had a viscosity of 4 poises at room temperature and was well dispersible in water or could be diluted with other paraffinic oils. On storage at 50° C, the product showed crystals of a diameter of 30 microns after 8 weeks and crystals having a diameter of 50 microns after 3 months. The solid matter, after this time, was only pooly dispersible in water and flocculated rapidly. The biological activity was heavily reduced.

EXAMPLE 14

There were ground as indicated in Example 1:
20 weight % of caboxine
4 weight % of Genapol X-080
9 weight % of Triton X-207
0.5 weight % of alizarin
0.5 weight % of aluminum acetate and
72 weight % of Essobayol 90.

During the grinding operation, the originally orange-yellow dispersion turned red. The dispersion had the same properties and the same stability to storage as the dispersion prepared according to Example 3. When in the Examples 10 to 14 the alizarine chelate component was not used, there was crystal growth during the storage as described in Example 9.

EXAMPLE 15

The wettable powders of the active substances according to Examples 1 to 7 used in the following biological Examples I and II were obtained by grinding mixtures having the following composition:
20.0 weight % of active substance
49.0 weight % of kaolinite containing quartz powder (Sillitin Z)
16.5 weight % of finely dispersed synthetic silicic acid (Wessalon S)
1.0 weight % sodium salt of oleymethyltauride (Hostapon T)
3.5 weight R of polypropyleneglycol
10.0 weight % sodium salt of ligninsulfonic acid.

BIOLOGICAL EXAMPLES

EXAMPLE I

Wheat plants (variety Jubilar) in the three leaf stage were heavily infested with spores of brown rust of wheat (*Puccinia triticina*) and placed dripping wet in a moisture chamber having a relative atmospheric humidity of 100% and a temperature of 20° C. After a residence time of 24 hours in this chamber, the plants were placed in a greenhouse and, 5 days later, treated until drip-off with oil dispersions of active substances according to Examples 1 to 7 (dispersed in water) in application amounts of 1000, 500, 250, 125, 60 and 30 mg each of active substance/liter of spray liquor. As comparative agents, the same compounds were used in the form of wettable powder formulations (see Example 15). After drying of the sprayed layer, the plants were again placed in the greenhouse, and, after the outbreak of the rust spots on the untreated infested control plants (14 days after inoculation), examined visually. The results of the examination listed in Table I show the rust infestation in %, relative to untreated infested control plants (= 100% infestation).

As Table I shows, the oil dispersions of the invention are significantly superior to the wettable powder formulations of the same active substances with respect to the fungicidal activity.

EXAMPLE II 8 to 9 days old bean plants (variety Angela) were treated until drip-off as indicated in Example I with the same oil dispersions according to Examples 1 to 7 in application amounts of 1000, 500, 250, 125, 60, 30 and 15 mg of active substance/liter of spray liquor. As comparative agents the same compounds in the form of wettable powders were used in the same application amounts.

After drying of the sprayed layer, the plants were heavily infested with spores of bean rust (*Uromyces phaseoli*) and placed dripping wet in a moisture chamber having a relative atmospheric humidity of 100% and a temperature of 20° C. After a residence time of 24 hours in the chamber, the plants were placed in a greenhouse (20° C, 70% of relative atmopsheric humidity). The evaluation of rust infestation was carried out visually after the outbreak of the rust spots on untreated infested control plants (12 days after inoculation). The results are listed in Table II and show the rust infestation in % relative to untreated infested control plants (= 100% infestation).

As Table II shows, the oil dispersions of the invention are significantly superior to the wettable powder formulations of the same active substances with respect to the fungicidal activity.

EXAMPLE III

Oat plants (variety Flamings Krone) in the three-leaf stage were treated until drip-off as indicated in Example II with oil dispersions of active substances according to Examples 1 to 7 in application amounts of 250, 125, 60, 30 and 15 mg each of active substance/liter of spray liquor. As comparative agents, the same compounds in the form of wettable powders were used in the same application amounts.

After drying of the sprayed layer, the plants were heavily infested with spores of crown rust of oats (*Puccinia corronifera*) (dry infestation) and subsequently placed for 24 hours in a moisture chamber having a relative atmospheric humidity of 100% and a temperature of 20° C. The plants were then kept in a greenhouse at 20° C and a relative atmospheric humidity of about 70%. After the outbreak of the rust spots on untreated infested control plants (12 days after inoculation), the results were evaluated visually. These results are listed in Table I and show the rust infestation in % relative to untreated infested control plants (= 100% infestation).

The results of Table III prove that the wettable powder formulations of the active substances are inferior to the oil dispersions with respect to their fungicidal activity.

Table I

| Compounds according to Example | % infestation with brown rust of wheat at mg of active substance/liter of spray liquor | | | | | |
|---|---|---|---|---|---|---|
| | 1000 | 500 | 250 | 125 | 60 | 30 |
| 1 as dispersion | 0 | 0 | 0 | 10 | 15 | 25 |
| 1 as wettable powder | 0 | 3 | 10 | 35 | 60 | 100 |
| 2 as dispersion | 0 | 0 | 0 | 3 | 15 | 25 |
| 2 as wettable powder | 0 | 0 | 5 | 25 | 35 | 60 |
| 3 as dispersion | 0 | 0 | 0 | 15 | 25 | 25 |
| 3 as wettable powder | 3 | 5 | 15 | 25 | 40 | 60 |
| 4 as dispersion | 0 | 0 | 0 | 0 | 5 | 25 |
| 4 as wettable powder | 0 | 3 | 5 | 10 | 35 | 60 |
| 5 as dispersion | 0 | 0 | 0 | 10 | 20 | 35 |
| 5 as wettable powder | 5 | 10 | 20 | 35 | 60 | 100 |
| 6 as dispersion | 0 | 0 | 5 | 15 | 25 | 35 |
| 6 as wettable powder | 5 | 15 | 35 | 60 | 100 | 100 |
| 7 as dispersion | 0 | 0 | 3 | 10 | 25 | 35 |
| 7 as wettable powder | 3 | 10 | 25 | 60 | 100 | 100 |
| untreated infested plants | 100 | 100 | 100 | 100 | 100 | 100 |

Table II

| Compounds according to Example | % of infestation with bean rust at mg of active substance/liter of spray liquor | | | | | | |
|---|---|---|---|---|---|---|---|
| | 1000 | 500 | 250 | 125 | 60 | 30 | 15 |
| 1 dispersion | 0 | 0 | 0 | 3 | 5 | 15 | 20 |
| 1 wettable powder | 0 | 0 | 3 | 5 | 10 | 15 | 25 |
| 2 dispersion | 0 | 0 | 0 | 0 | 3 | 5 | 10 |
| 2 wettable powder | 0 | 0 | 3 | 5 | 10 | 15 | 25 |
| 3 dispersion | 0 | 0 | 0 | 3 | 5 | 10 | 15 |
| 3 wettable powder | 0 | 0 | 0 | 3 | 10 | 25 | 35 |
| 4 dispersion | 0 | 0 | 0 | 0 | 0 | 0 | 3 |
| 4 wettable powder | 0 | 0 | 0 | 0 | 3 | 5 | 15 |
| 5 dispersion | 0 | 0 | 0 | 3 | 5 | 10 | 15 |
| 5 wettable powder | 0 | 0 | 3 | 5 | 10 | 15 | 25 |
| 6 dispersion | 0 | 0 | 0 | 0 | 3 | 10 | 15 |
| 6 wettable powder | 0 | 0 | 3 | 5 | 15 | 25 | 60 |
| 7 dispersion | 0 | 0 | 0 | 0 | 0 | 3 | 5 |
| 7 wettable powder | 0 | 0 | 0 | 3 | 5 | 15 | 35 |
| untreated infested plants | 100 | 100 | 100 | 100 | 100 | 100 | 100 |

Table III

| Compounds according to Example | % infestation with crown rust of oats at mg of active substance/liter of spray liquor | | | | |
|---|---|---|---|---|---|
| | 250 | 120 | 60 | 30 | 15 |
| 1 as dispersion | 0 | 0 | 5 | 10 | 15 |
| 1 as wettable powder | 3 | 5 | 15 | 26 | 35 |
| 2 as dispersion | 0 | 0 | 3 | 5 | 10 |
| 2 as wettable powder | 0 | 3 | 5 | 15 | 25 |
| 3 as dispersion | 0 | 3 | 5 | 15 | 20 |
| 3 as wettable powder | 3 | 5 | 10 | 15 | 25 |
| 4 as dispersion | 0 | 0 | 0 | 3 | 5 |
| 4 as wettable powder | 0 | 3 | 5 | 15 | 25 |
| 5 as dispersion | 0 | 3 | 5 | 15 | 20 |
| 5 as wettable powder | 5 | 10 | 15 | 35 | 60 |
| 6 as dispersion | 0 | 0 | 3 | 5 | 15 |
| 6 as wettable powder | 0 | 3 | 5 | 10 | 15 |
| 7 as dispersion | 0 | 0 | 0 | 3 | 10 |
| 7 as wettable powder | 0 | 3 | 5 | 10 | 25 |
| untreated infested plants | 100 | 100 | 100 | 100 | 100 |

EXAMPLE IV

The dispersions according to Examples 9 to 14 were used for combating the anthracnose of beans in a greenhouse test. For this purpose, dwarf bush beans were infested in the early primary leaf stage with conidia of anthracnose of beans (*Colletotrichum lindemuthianum*) and placed dripping wet for 24 hours in a moisture chamber having a relative atmospheric humidity of 100% and a temperature of 18° C. Subsequently, they are placed in a greenhouse having a relative atmospheric humidity of 80 - 90%, and, 3 days after the infestation, they were treated until drip-off with the products in aqueous suspension and in application amounts of 500, 250 and 125 mg of active substance per liter of spray liquor. For a comparison, infested plants were treated with commercial wettable powder formulations of carboxine and oxycarboxine having a content of 50% of active substance in the same application concentrations. After drying of the sprayed layer, the plants were placed again in the greenhouse and, 21 days after the infestation, examined for anthracnose. As results from Table IV, the formulations according to this invention are very active against anthracnose, while the commercial wettable powder formulation practically had no effect whatsoever.

Table IV

| Product according to Example | % infestation with Colletotrichum in beans at mg of active substance/liter of spray liquor | | |
|---|---|---|---|
| | 500 | 250 | 125 |
| 9 (freshly prepared) | 0 | 0 | 18 |
| 10 (freshly prepared) | 0 | 0 | 12 |
| 11 (3 months storage at 50° C) | 0 | 0 | 13 |
| 12 (3 months storage at 50° C) | 0 | 0 | 10 |
| 13 | | | |
| 14 | | | |
| commercial formulation of oxycarboxine | 43 | 63 | 80 |
| commercial formulation of carboxine | | | |
| untreated infested plants | 100 | 100 | 100 |

EXAMPLE V

The dispersions according to Examples 9 to 14 were used for the curative treatment of rust diseases of wheat. For this purpose, wheat plants in the three-leaf stage were heavily infested with brown rust of wheat and placed dripping wet for 24 hours in a moisture chamber having a temperature of 20° C and an atmospheric humidity of 100%. Subsequently, the infested plants were put into a greenhouse having a temperature of 20° C. After an infection time of 5 days, the plants were treated until drip-off with the products according to Examples 9 to 14 in application amounts of 500, 250, 125 and 60 mg of active substance per liter of spray liquor. As comparative agents, commercial wettable powder formulations of oxycarboxine and carboxine were used in the same application concentrations. After an incubation time of 14 days, the plants were examined for brown rust. The results are listed in Table V as compared to untreated infested plants.

Table V

| Product according to Example | % infestation with brown rust of wheat at mg of active substance/liter of spray liquor | | | |
|---|---|---|---|---|
| | 500 | 250 | 125 | 60 |
| 9 (freshly prepared) | 0 | 0 | 0 | 15 |
| 10 (freshly prepared) | 0 | 0 | 0 | 8 |
| 10 (3 months storage at 50° C) | 0 | 0 | 0 | 10 |
| 11 (freshly prepared) | 0 | 0 | 0 | 10 |
| 12 (freshly prepared) | 0 | 0 | 0 | 10 |
| 13 | | | | |
| 14 | | | | |

Table V-continued

| Product according to Example | % infestation with brown rust of wheat at mg of active substance/ liter of spray liquor | | | |
|---|---|---|---|---|
| | 500 | 250 | 125 | 60 |
| commercial formulations of oxycarboxine | 0 | 0 | 18 | 30 |
| commercial formulation of carboxine | | | | |
| untreated infested plants | 100 | 100 | 100 | 100 |

EXAMPLE VI

The dispersions of Examples 9 to 14 were used for the following tests:

Young coffee plants, at a height of 15 cm, were heavily infested with spores of coffee rust (*Hemileia vastatrix*) and subsequently placed dripping wet for 3 days in a moisture chamber having a temperature of 22° C and a relative atmospheric humidity of 100%. Subsequently, they were placed in a greenhouse having a temperature of 22°-23° C and a relative atmospheric humidity of 85-95%. After an infection time of 5 days, the plants were treated until drip-off with the formulations of the invention in application amounts of 500, 250, 125 and 60 mg of active substance per liter of spray liquor. As comparative agents, commercial wettable powder formulations of oxycarboxine and carboxine were used in the same concentrations of active substance.

After drying of the sprayed layer, 50 samples each having a 3 × 3 cm dimension were cut out of the leaves, 10 of them each were placed with their upper side on wet filter paper in glass dishes and again infested with conidia of coffee rust by putting them dropwise on the leaves. These 5 moisture dishes of one concentration each were covered and placed in the greenhouse at 22° C.

After an incubation time of 4 months, the samples of leaves were examined for coffee rust infestation. The results are listed in Table VI in comparison to untreated infested samples of leaves. The formulations of the invention show a considerably better activity against coffee rust than commercial wettable powder formulations.

Table VI

| Product according to Example | % infestation with coffee rust at mg of active substance/liter of spray liquor | | | |
|---|---|---|---|---|
| | 500 | 250 | 125 | 60 |
| 9 (freshly prepared) | 0 | 0 | 0 | 18 |
| 10 (freshly prepared) | 0 | 0 | 0 | 10 |
| 10 (3 months storage at 50° C) | 0 | 0 | 0 | 12 |
| 11 (freshly prepared) | 0 | 0 | 0 | 12 |
| 12 (freshly prepared) | 0 | 0 | 0 | 12 |
| 13 | | | | |
| 14 | | | | |
| commercial form of oxycarboxine / carboxine | 0 | 10 | 28 | 42 |
| untreated infested plants | 100 | 100 | 100 | 100 |

What is claimed is:

1. A fungicidal dispersion comprising from 0.2 to 5 percent, by weight of said dispersion, of an aluminum chelate of a polynuclear hydroxy-quinone selected from the group consisting of naphthazarin, quinizarin, chrysazin, and alizarin present in said dispersion as a stabilizer discouraging crystal growth of the fungicidally-active ingredient, said dispersion comprising, as the fungicidally-active ingredient, from 5 to 50 percent by weight of a compound of the formula

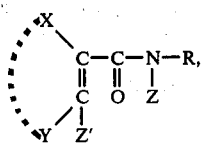

wherein X and Y, together with the —C═C— group, form a partially unsaturated or totally unsaturated five- or six-membered carbocyclic or heterocyclic ring system selected from the group consisting of unsubstituted furan, pyran, dihydrofuran, dihydropyran, oxazole, triazole, thiadiazole, thiazole, dioxane, dithiane, 4H-thiapyran, 4H-thiapyran dioxide, 4H-thiapyran monoxide, 5,6-dihyro-1,4-oxathiine, 5,6-dihydro-oxathiine-4,4-dioxide, pyridine, cyclopentene, cyclohexene, norbornadiene, and phenyl, and such ring systems which, in addition to substituent Z', are substituted with at least halogen, alkyl having 1 to 4 carbon atoms, alkoxy having 1 to 4 carbon atoms, oxymethylene, or phenyl; Z' is hydrogen, halogen, or alkyl having 1 to 4 carbon atoms; Z is hydrogen, straight or branched alkyl having 1 to 6 carbon atoms, or straight or branched haloalkyl having from 1 to 6 carbon atoms; and R is

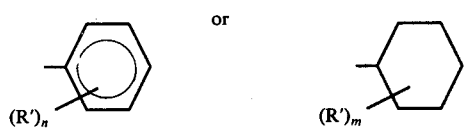

wherein R' is dioxymethylene or the same or different alkyl or alkoxy having 1 to 4 carbon atoms, $m$ is an integer from 0 to 3, and $n$ is an integer from 0 to 3 or, if

is dihydropyran and Z is methyl, then $n$ is integer from 1 to 3, said fungicidally-active ingredient being dispersed in at least one member selected from the group consisting of $C_8$ to $C_{25}$ paraffinic mineral oils boiling at a temperature above 140° C.; rape-seed oil; arachis oil; sunflower oil; cotton seed oil; liquid monoesters and diesters formed between $C_1$ to $C_{12}$ monoalcohols and $C_2$ to $C_{10}$ monobasic and dibasic carboxylic acids, and monoesters having from 8 to 12 carbon atoms and said diesters having at most 32 carbon atoms.

2. A stabilized fungicidal dispersion as in claim 1, wherein said fungicidally-active ingredient is dispersed in a liquid diester of phthalic acid.

3. A stabilized fungicidal dispersion as in claim 2 wherein said liquid diester is phthalic acid di-iso-octyl ester.

4. A stabilized fungicidal dispersion as in claim 1 wherein said stabilizer is the aluminum chelate of alizarin.

5. A stabilized fungicidal dispersion as in claim 1 which comprises from 15 to 30 percent by weight of said fungicidally-active ingredient.

6. A stabilized fungicidal dispersion as in claim 1 which comprises from 0.4 to 2 percent by weight of said aluminum chelate stabilizer.

7. A stabilized fungicidal dispersion as in claim 1 wherein said aluminum chelate is formed in situ in said dispersion from said polynuclear hydroxy-quinone and aluminum hydroxide or an aluminum salt.

8. A stabilized fungicidal composition as in claim 1 which comprises up to 25 percent, by weight of said dispersion, of an emulsifier.

* * * * *